(12) United States Patent
Willard (10) Patent No.: US 10,398,548 B2
(45) Date of Patent: Sep. 3, 2019

(54) DELIVERY SYSTEM DEFLECTION MECHANISM

(71) Applicant: St. Jude Medical, Cardiology Division, Inc., St. Paul, MN (US)

(72) Inventor: Steven N. Willard, Bloomington, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 225 days.

(21) Appl. No.: 15/350,251

(22) Filed: Nov. 14, 2016

(65) Prior Publication Data
US 2017/0056168 A1 Mar. 2, 2017

Related U.S. Application Data

(62) Division of application No. 13/790,132, filed on Mar. 8, 2013, now Pat. No. 9,532,871.
(Continued)

(51) Int. Cl.
*A61F 2/24* (2006.01)
*A61M 25/01* (2006.01)
*A61M 25/00* (2006.01)

(52) U.S. Cl.
CPC .......... *A61F 2/2427* (2013.01); *A61F 2/2436* (2013.01); *A61M 25/0074* (2013.01); *A61M 25/0133* (2013.01); *A61F 2250/0029* (2013.01)

(58) Field of Classification Search
CPC . A61F 2/2427; A61F 2/2436; A61M 25/0074; A61M 25/0133
See application file for complete search history.

(56) References Cited

U.S. PATENT DOCUMENTS 3,384,088 A 5/1968 Miseo
3,657,744 A 4/1972 Ersek
(Continued)

FOREIGN PATENT DOCUMENTS

EP 1129744 A1 9/2001
EP 1157673 A2 11/2001
(Continued)

OTHER PUBLICATIONS

Ruiz, Carlos, Overview of PRE-CE Mark Transcatheter Aortic Valve Technologies, Euro PCR, May 25, 2010.
(Continued)

*Primary Examiner* — Tuan V Nguyen
(74) *Attorney, Agent, or Firm* — Lerner, David, Littenberg, Krumholz & Mentlik, LLP (57) ABSTRACT

A delivery device for a prosthetic heart valve includes a proximal sheath and a distal sheath. The proximal sheath has a distal end disposed at an oblique angle relative to the longitudinal axis of the proximal sheath, and the distal sheath has a proximal end disposed at an oblique angle relative to the longitudinal axis of the distal sheath. The distal end of the proximal sheath and the proximal end of the distal sheath mate so that rotation of the distal sheath relative to the proximal sheath causes the distal sheath to deflect from coaxial alignment with the proximal sheath. Deflection of the distal sheath relative to the proximal sheath enables the prosthetic valve to be axially aligned with the native valve annulus for deployment.

21 Claims, 6 Drawing Sheets

Related U.S. Application Data (60) Provisional application No. 61/642,889, filed on May 4, 2012.

(56) References Cited

U.S. PATENT DOCUMENTS

| | | | |
|---|---|---|---|
| 3,724,238 | A | 4/1973 | Retali et al. |
| 4,423,730 | A | 1/1984 | Gabbay |
| 4,641,657 | A | 2/1987 | Ellis |
| 5,368,592 | A | 11/1994 | Stern et al. |
| 5,372,587 | A | 12/1994 | Hammerslag et al. |
| 5,405,344 | A | 4/1995 | Williamson et al. |
| 5,507,725 | A | 4/1996 | Savage et al. |
| 5,549,594 | A | 8/1996 | Brunken |
| 5,569,270 | A | 10/1996 | Weng |
| 5,575,799 | A | 11/1996 | Bolanos et al. |
| 5,749,881 | A | 5/1998 | Sackier et al. |
| 5,843,167 | A | 12/1998 | Dwyer et al. |
| 5,868,685 | A | 2/1999 | Powell et al. |
| 5,924,424 | A | 7/1999 | Stevens et al. |
| 5,968,068 | A | 10/1999 | Dehdashtian et al. |
| 6,077,297 | A | 6/2000 | Robinson et al. |
| 6,183,432 | B1 | 2/2001 | Milo |
| 6,306,141 | B1 | 10/2001 | Jervis |
| 6,464,684 | B1 | 10/2002 | Galdonik |
| 6,599,237 | B1 | 7/2003 | Singh |
| 6,623,518 | B2 | 9/2003 | Thompson et al. |
| 6,743,239 | B1 | 6/2004 | Kuehn et al. |
| 6,814,746 | B2 | 11/2004 | Thompson et al. |
| 6,830,584 | B1 | 12/2004 | Seguin |
| 7,018,406 | B2 | 3/2006 | Seguin et al. |
| 7,300,431 | B2 | 11/2007 | Dubrovsky |
| 7,311,730 | B2 | 12/2007 | Gabbay |
| 7,510,572 | B2 | 3/2009 | Gabbay |
| 7,637,905 | B2 | 12/2009 | Saadat et al. |
| 7,682,390 | B2 | 3/2010 | Seguin |
| 7,803,185 | B2 | 9/2010 | Gabbay |
| 7,811,277 | B2 | 10/2010 | Boulais |
| 9,227,990 | B2 | 1/2016 | Phull et al. |
| 9,414,915 | B2 * | 8/2016 | Lombardi ............ A61F 2/2418 |
| 2003/0050694 | A1 | 3/2003 | Yang et al. |
| 2003/0233108 | A1 | 12/2003 | Gellman et al. |
| 2004/0210304 | A1 | 10/2004 | Seguin et al. |
| 2005/0137622 | A1 | 6/2005 | Griffin |
| 2005/0137695 | A1 | 6/2005 | Salahieh et al. |
| 2005/0137697 | A1 | 6/2005 | Salahieh et al. |
| 2005/0165352 | A1 | 7/2005 | Henry et al. |
| 2005/0177138 | A1 | 8/2005 | Dubrovsky |
| 2005/0222604 | A1 | 10/2005 | Schaeffer |
| 2006/0058872 | A1 | 3/2006 | Salahieh et al. |
| 2006/0074484 | A1 | 4/2006 | Huber |
| 2006/0100687 | A1 | 5/2006 | Fahey et al. |
| 2006/0106415 | A1 | 5/2006 | Gabbay |
| 2006/0142848 | A1 | 6/2006 | Gabbay |
| 2006/0167468 | A1 | 7/2006 | Gabbay |
| 2006/0235502 | A1 | 10/2006 | Belluche et al. |
| 2006/0259120 | A1 | 11/2006 | Vongphakdy et al. |
| 2007/0010876 | A1 | 1/2007 | Salahieh et al. |
| 2007/0027534 | A1 | 2/2007 | Bergheim et al. |
| 2007/0043259 | A1 | 2/2007 | Jaffe et al. |
| 2007/0043435 | A1 | 2/2007 | Seguin et al. |
| 2007/0055358 | A1 | 3/2007 | Krolik et al. |
| 2007/0073376 | A1 | 3/2007 | Krolik et al. |
| 2007/0073391 | A1 | 3/2007 | Bourang et al. |
| 2007/0088431 | A1 | 4/2007 | Bourang et al. |
| 2007/0112422 | A1 | 5/2007 | Dehdashtian |
| 2007/0162100 | A1 | 7/2007 | Gabbay |
| 2007/0168013 | A1 | 7/2007 | Douglas |
| 2007/0203575 | A1 | 8/2007 | Forster et al. |
| 2007/0239271 | A1 | 10/2007 | Nguyen |
| 2007/0244552 | A1 | 10/2007 | Salahieh et al. |
| 2007/0250113 | A1 | 10/2007 | Hegeman et al. |
| 2008/0065122 | A1 | 3/2008 | Stack et al. |
| 2008/0071369 | A1 | 3/2008 | Tuval et al. |
| 2008/0147160 | A1 | 6/2008 | Ghione et al. |
| 2008/0147182 | A1 | 6/2008 | Righini et al. |
| 2008/0228223 | A1 | 9/2008 | Alkhatib |
| 2009/0054975 | A1 | 2/2009 | del Nido et al. |
| 2009/0062606 | A1 | 3/2009 | Ueda et al. |
| 2009/0062839 | A1 | 3/2009 | Kurrus |
| 2010/0004740 | A1 | 1/2010 | Seguin et al. |
| 2010/0204708 | A1 | 8/2010 | Sharma |
| 2010/0228152 | A1 | 9/2010 | Fisher et al. |
| 2010/0228191 | A1 | 9/2010 | Alvarez et al. |
| 2010/0286768 | A1 | 11/2010 | Alkhatib |
| 2010/0298931 | A1 | 11/2010 | Quadri et al. |
| 2011/0098800 | A1 | 4/2011 | Braido et al. |
| 2011/0207999 | A1 | 8/2011 | Torisawa et al. |
| 2011/0224678 | A1 | 9/2011 | Gabbay |
| 2011/0245917 | A1 | 10/2011 | Savage et al. |
| 2012/0078350 | A1 | 3/2012 | Wang et al. |
| 2012/0303111 | A1 | 11/2012 | Dwork et al. |
| 2013/0060328 | A1 | 3/2013 | Rothstein |
| 2013/0103047 | A1 | 4/2013 | Steingisser et al. |
| 2013/0274870 | A1 | 10/2013 | Lombardi et al. |
| 2013/0297012 | A1 | 11/2013 | Willard |
| 2013/0297102 | A1 | 11/2013 | Hughes et al. |

FOREIGN PATENT DOCUMENTS

| | | |
|---|---|---|
| EP | 1716822 A1 | 11/2006 |
| EP | 1926455 A2 | 6/2008 |
| FR | 2765098 A1 | 12/1998 |
| WO | 9510317 A1 | 4/1995 |
| WO | 2006138173 A2 | 12/2006 |
| WO | 07071436 A2 | 6/2007 |
| WO | 08070797 A2 | 6/2008 |
| WO | 10051025 A1 | 5/2010 |
| WO | 10087975 A1 | 8/2010 |
| WO | 2010127162 A1 | 11/2010 |
| WO | 2012112469 A2 | 8/2012 |
| WO | 2013166355 A1 | 11/2013 |
| WO | 2014130160 A1 | 8/2014 |

OTHER PUBLICATIONS

Quaden, Rene, et al., Percutaneous aortic valve replacement: resection before implantation, 836-840, European J. of Cardio-thoracic Surgery, 27 (2005).

International Search Report for Application No. PCT/US2013/078306 dated May 2, 2014.

International Search Report and Written Opinion for Application No. PCT/US2013/039405 dated Sep. 23, 2013.

International Search Report and Written Opinion for Application No. PCT/US2014/054025 dated Nov. 19, 2014.

International Search Report and Written Opinion for Application No. PCT/US2014/055053 dated Nov. 24, 2014.

* cited by examiner

DELIVERY SYSTEM DEFLECTION MECHANISM

CROSS-REFERENCE TO RELATED APPLICATIONS

The present application is a divisional of U.S. patent application Ser. No. 13/790,132 filed Mar. 8, 2013, now U.S. Pat. No. 9,532,871, which claims the benefit of U.S. Provisional Patent Application No. 61/642,889 filed May 4, 2012, the disclosures of which are hereby incorporated herein by reference.

BACKGROUND OF THE INVENTION

The present invention is related to heart valve replacement, and more particularly to devices, systems, and methods for transcatheter delivery of collapsible prosthetic heart valves.

Prosthetic heart valves that are collapsible to a relatively small circumferential size may be delivered into a patient less invasively than valves that are not collapsible. For example, a collapsible valve may be delivered into a patient via a tube-like delivery apparatus such as a catheter, a trocar, a laparoscopic instrument, or the like. This collapsibility may avoid the need for a more invasive procedure such as full open-chest, open-heart surgery.

Collapsible prosthetic heart valves typically take the form of a valve structure mounted on a stent. To place such a valve into a delivery apparatus and ultimately into a patient, the valve must first be collapsed or crimped to reduce its circumferential size. For example, a conventional collapsible prosthetic valve is typically collapsed and retained in a collapsed state by a sheath for delivery into the patient, for example, through a femoral artery or through the apex of the heart.

An end of a guide wire may be inserted percutaneously into the artery or the heart of a patient just beyond a desired implant site to establish a guide for an implantable delivery device to follow. The desired implant site is often at or near the annulus of the patient's heart valve that is to be replaced by the prosthetic valve. Once the delivery apparatus containing the prosthetic valve has reached this site, the valve may be deployed or released from the delivery apparatus and re-expanded to full operating size. For self-expanding valves, the stent automatically begins to expand as the sheath covering the valve is withdrawn.

In certain transapical delivery systems employing self-expanding aortic valves, for example, after the delivery system has been positioned for deployment, the annulus end of the valve may be unsheathed and expanded first, while the aortic end of the valve remains sheathed. Once the annulus end of the valve has expanded, it may be determined that the valve needs to be repositioned in the patient's aortic annulus. To accomplish this, the user (such as a surgeon or an interventional cardiologist) may resheath the annulus end of the valve so that the valve can be repositioned while in a collapsed state. After the valve has been repositioned, the user can again deploy the valve.

Despite the various improvements that have been made to the collapsible prosthetic heart valve delivery process, conventional delivery devices, systems, and methods suffer from some shortcomings. For example, in a conventional delivery device for collapsible prosthetic valves, such as a transapical delivery device 7 shown in FIG. 1, because the aortic valve is not directly aligned with the apex of the heart, it may be difficult to align the longitudinal axis of the distal sheath 8 normally to the geometric center of the native valve annulus 6 (i.e., axial alignment). Without axial alignment, the user will be unable to properly position the prosthetic valve relative to the native annulus 6, such that the valve will not be properly seated in the annulus and therefore will not function properly. Moreover, without axial alignment, the inner wall 3 of the aortic arch 2 may interfere with the advancement of delivery device 7 beyond the native valve annulus 6, and contact between the distal tip 9 of the delivery device and the inner wall of the aortic arch may damage the aorta.

There is therefore a need for further improvements to the devices, systems, and methods for transcatheter delivery of collapsible prosthetic heart valves. Among other advantages, the present invention may address one or more of these needs.

BRIEF SUMMARY OF THE INVENTION

One aspect of the present invention provides a device for delivering a medical implant into a patient. One embodiment of the delivery device includes a first sheath having a proximal end, a distal end and a longitudinal axis, the distal end having a surface disposed at an oblique angle relative to the longitudinal axis of the proximal sheath; and a distal sheath connected to the distal end of the proximal sheath, the distal sheath having a proximal end, a distal end and a longitudinal axis. The proximal end of the distal sheath has a surface disposed at an oblique angle relative to the longitudinal axis of the distal sheath, the proximal end surface of the distal sheath being in mating engagement with the distal end surface of the proximal sheath. The distal sheath is rotatable relative to the proximal sheath from a first position in which the longitudinal axis of the distal sheath is substantially coaxial with the longitudinal axis of the proximal sheath, to a second position in which the longitudinal axis of the distal sheath is oriented at an oblique angle to the longitudinal axis of the proximal sheath. The oblique angle at which the distal end surface of the proximal sheath is oriented is preferably the same as the oblique angle at which the proximal end surface of the distal sheath is oriented. The distal sheath may be rotated by at least about 180° from the first position to the second position. An atraumatic tip may be connected to the distal end of the distal sheath.

The proximal sheath may be rotatably connected to the distal sheath by an axle. One end of the axle may be fixedly connected to one of the proximal sheath or distal sheath, while the other end of the axle may be rotatably connected to the other of the proximal sheath or distal sheath. Alternatively, both ends of the axle may be rotatably connected to the respective sheaths. Rather than an axle, the proximal sheath may be connected to the distal sheath by a ball-and-socket connection.

The device may further include a locking mechanism having a first position permitting rotation of the distal sheath relative to the proximal sheath, and a second position preventing rotation of the distal sheath relative to the proximal sheath. The locking mechanism may include an elongated member movable in the proximal sheath between a retracted position and an extended position, and at least one recess in the distal sheath, the elongated member in the extended position being receivable in the recess to prevent rotation of the distal sheath relative to the proximal sheath, and the elongated member in the retracted position being free of the recess to permit rotation of the distal sheath relative to the proximal sheath. A spring may be disposed on the elongated member for biasing the elongated member to the extended position.

The proximal sheath may include a lumen extending between the proximal end of the proximal sheath and the distal end of the proximal sheath, and the distal sheath may include a lumen extending between the proximal end of the distal sheath and the distal end of the distal sheath, the lumen of the proximal sheath being in communication with the lumen of the distal sheath.

One or both of the distal end surface of the proximal sheath and the proximal end surface of the distal sheath may be flat, curvate, hemispheroidal, or any other desired shape.

Another aspect of the present invention provides a method for implanting a prosthetic heart valve into a patient. The method includes inserting a delivery device into the patient, the delivery device including a proximal sheath, a distal sheath and a prosthetic heart valve assembled in the distal sheath. The proximal sheath has a proximal end, a distal end and a longitudinal axis, the distal end having a surface disposed at an oblique angle relative to the longitudinal axis of the proximal sheath. The distal sheath is connected to the distal end of the proximal sheath, and has a proximal end, a distal end and a longitudinal axis. The proximal end of the distal sheath has a surface disposed at an oblique angle relative to the longitudinal axis of the distal sheath, the proximal end surface of the distal sheath being in mating engagement with the distal end surface of the proximal sheath. The method further includes rotating the distal sheath relative to the proximal sheath to orient the longitudinal axis of the distal sheath at an oblique angle to the longitudinal axis of the proximal sheath; and deploying the prosthetic heart valve from the distal sheath.

The proximal sheath may have a lumen extending from the proximal end of the proximal sheath to the distal end of the proximal sheath, and the distal sheath may have a lumen extending from the proximal end of the distal sheath to the distal end of the distal sheath. In such event, the method may further include inserting a guidewire into the patient; and inserting the delivery device over the guidewire by passing the guidewire through the lumen in the distal sheath and the lumen in the proximal sheath.

BRIEF DESCRIPTION OF THE DRAWINGS

Various embodiments of the present invention will now be discussed with reference to the appended drawings. It is to be appreciated that these drawings depict only some embodiments of the invention and are therefore not to be considered limiting of its scope.

DETAILED DESCRIPTION

In the present application, reference is made to particular features of the invention. It is to be understood that the disclosure of the invention in this application is intended to include all possible combinations of such features, whether or not such combinations have been particularly described. For example, where a feature is disclosed in the context of a particular aspect, arrangement, or embodiment of the invention, that feature can also be used, to the extent possible, in combination with and/or in the context of other aspects, arrangements, and embodiments of the invention described herein.

The term "comprises" and grammatical equivalents thereof are used herein to mean that other components, ingredients, steps, etc. are optionally present. For example, an article "comprising" (or "which comprises") components A, B, and C can consist of (i.e., contain) only components A, B, and C, or can consist of not only components A, B, and C, but also one or more other components. The term "step of" does not mean "step for".

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all of the defined steps (except where the context excludes that possibility).

The term "at least" followed by a number is used herein to denote the start of a range beginning with that number (which can be a range having an upper limit or no upper limit, depending on the variable being defined). For example, "at least 1" means 1 or more than 1.

As used herein, the terms "proximal" and "distal" are to be taken as relative to a user (e.g., a surgeon or an interventional cardiologist) of the disclosed delivery devices. "Proximal" is to be understood as relatively close to the user and "distal" is to be understood as relatively farther away from the user.

As described further herein, a device for delivering collapsible prosthetic heart valves (or other types of collapsible stents) in accordance with the present invention may include a catheter having proximal and distal portions, the longitudinal axis of the distal portion being substantially coaxial with the longitudinal axis of the proximal portion in one position, and being oriented at varying oblique angles to the longitudinal axis of the proximal portion in other positions to enable the device to deliver a prosthetic heart valve in substantial axial alignment with the native annulus in which the valve is to be deployed.

Figure 2:
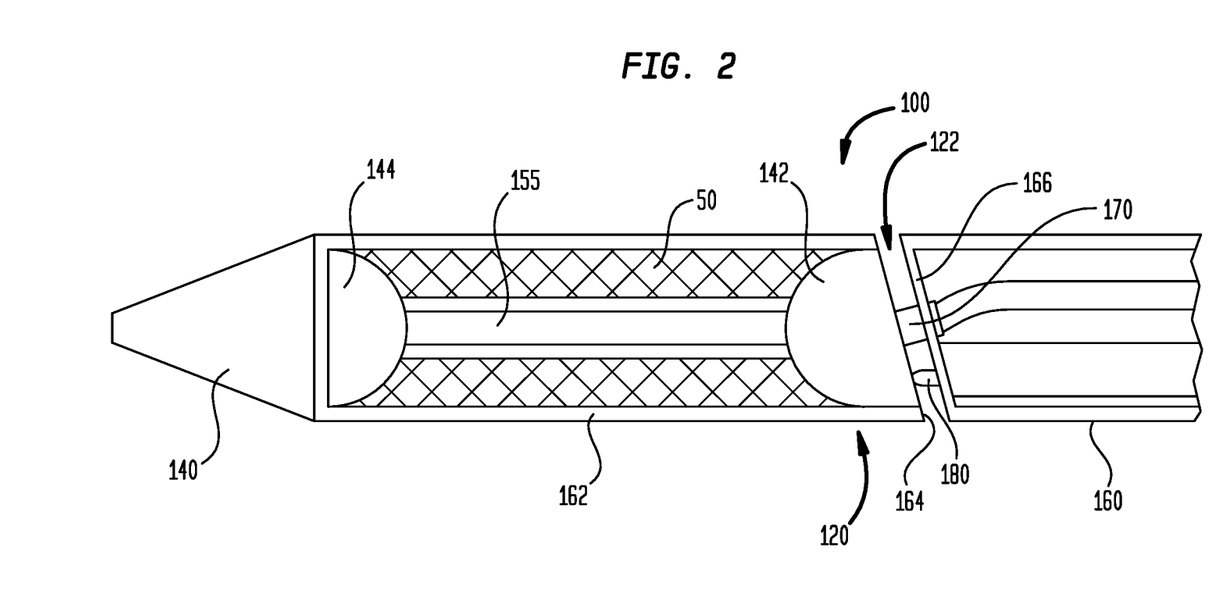
FIG. 2 is a plan view of a distal portion of a delivery device in accordance with one embodiment of the present invention, shown in partial cross-section in a substantially straight configuration.
Figure 3:
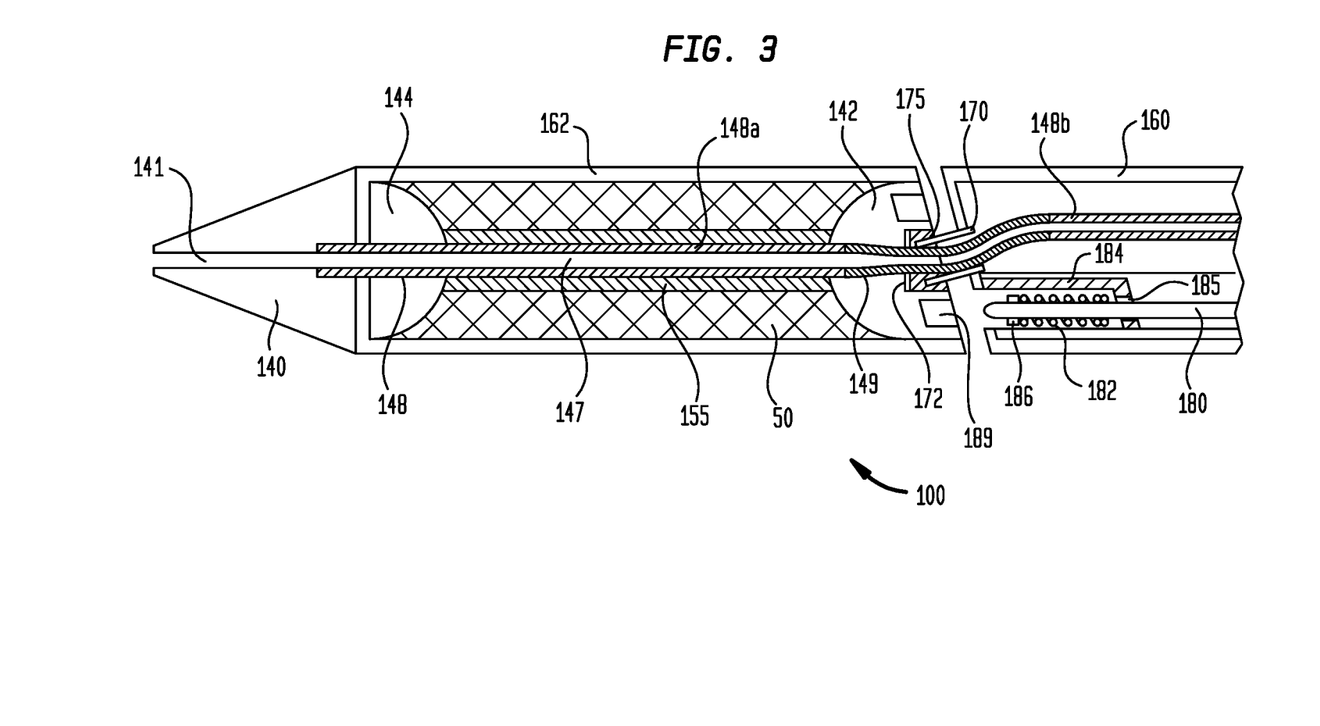
FIG. 3 is a cross-sectional plan view of the distal portion of the delivery device of FIG. 2, shown in the substantially straight configuration.
Figure 4:
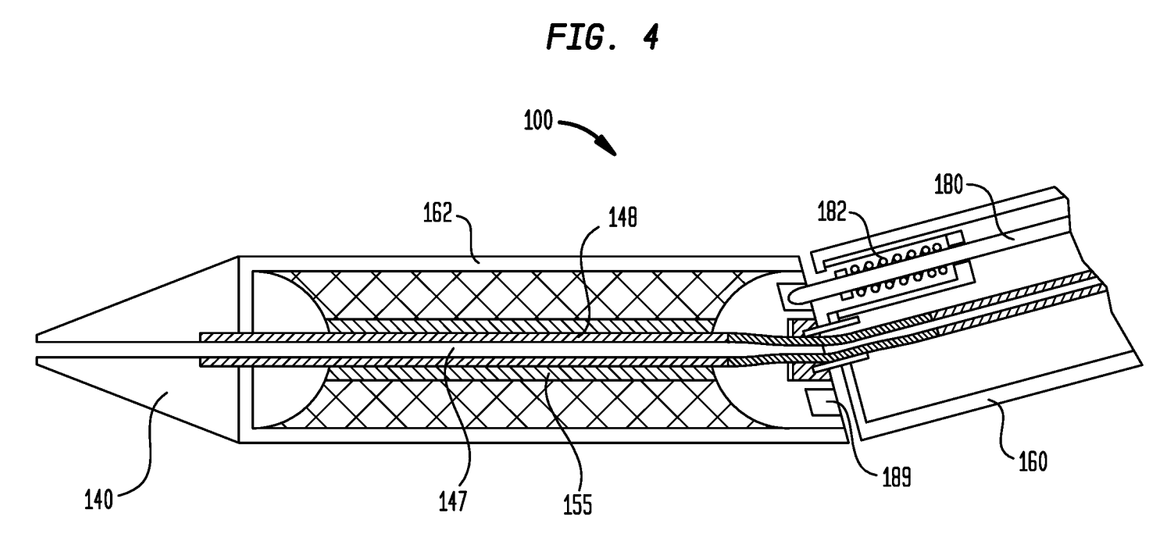
FIG. 4 is a cross-sectional plan view of the distal portion of the delivery device of FIG. 2, shown in a deflected configuration.

Referring now to FIGS. 2-4, in one embodiment of the invention, a delivery device 100 may include a hollow elongated sheath 120 having a longitudinal axis extending between its proximal end (not shown) and its distal end. The sheath 120 may have a circular cross-section as shown, or any other cross-section as desired, such as an elliptical cross-section. Sheath 120 may have a "split sheath" configuration, i.e., it may be separated, as at 122, into a proximal sheath 160 and a distal sheath 162. As will be explained below, the distal sheath 162 may be moved distally relative to the proximal sheath 160 in order to deploy the prosthetic valve.

At its distal end, device 100 may include a proximal retainer 142 and a distal retainer 144 spaced apart by a hollow shaft 155 so as to define a receiving compartment therebetween. An implantable device, such as a collapsible prosthetic heart valve 50, may be mounted in the receiving compartment around shaft 155. As illustrated in FIGS. 2-4, the distal sheath 162 may act as a covering over the valve 50. The distal end of the proximal sheath 160 may be closed by an end wall 166 disposed at an oblique angle relative to the longitudinal axis of the proximal sheath. The proximal end 164 of the distal sheath 162 may similarly be disposed at an oblique angle relative to the longitudinal axis of the distal sheath, but is not enclosed by an end wall so that the distal sheath is able to move distally to deploy valve 50. Preferably, the proximal end 164 of distal sheath 162 will be oriented at substantially the same angle as the end wall 166 of proximal sheath 160. In a variant hereof, the proximal end 164 of distal sheath 162 may be closed by the proximal retainer 142. In such event, the proximal surface of proximal retainer 142 may lie at an oblique angle to the longitudinal axis of distal sheath 162 so as to lie in the same plane as the proximal end 164 of the distal sheath. Although sheath end wall 166 and the proximal end 164 of distal sheath 162 are depicted as planar, they may be curvate, hemispheroidal or any other desired shape.

An atraumatic tip 140 formed from a soft polymer may be fixedly connected to the distal end of distal sheath 162. The tip 140 may have a cross-section that matches the cross-section of distal sheath 162. An inner tubular shaft 148 may be connected at one end to tip 140, and may extend through hollow shaft 155 and through proximal sheath 160 to the proximal end thereof. Shaft 148 has a central lumen 147 which communicates with a bore 141 extending longitudinally through tip 140. Lumen 147 and bore 141 together define a channel through device 100 for a guidewire (not shown). Preferably, lumen 147 remains patent through shaft 148 whether the longitudinal axes of proximal sheath 160 and distal sheath 162 are coaxially aligned, or are disposed at an oblique angle to one another, thereby enabling device 100 to be advanced over the guidewire in either a coaxial or angularly deflected configuration. Pushing inner shaft 148 in a distal direction will cause distal sheath 162 to slide distally to an open position relative to proximal sheath 160, and pulling inner shaft 148 in a proximal direction will cause the distal sheath to slide proximally to a closed position relative to the proximal sheath.

In the fully closed position, the distal sheath 162 may be in a proximalmost position covering the valve 50 with its proximal end 164 abutting the end wall 166 of the proximal sheath 160. In the fully opened position, the distal sheath 162 may be in a distalmost position with its proximal end 164 spaced from the end wall 166 of the proximal sheath to expose the prosthetic valve 50 for deployment. Although the figures illustrate a gap between the proximal end 164 of distal sheath 162 and end wall 166 in the closed position of the distal sheath, that gap is merely for the purpose of illustrating the various components of device 100. Thus, in the fully closed position, the proximal end 164 of distal sheath 162 and end wall 166 will preferably be in abutting relationship as will be described further below.

The proximal sheath 160 and the distal sheath 162 may be connected by a tubular axle 170. As clearly seen in FIG. 2, the longitudinal axis of axle 170 preferably is oriented substantially perpendicular to sheath ends 164 and 166 so as to not interfere with the rotation of sheaths 160 and 162 relative to one another. The central bore extending through axle 170 has a diameter sufficient to slidably receive inner shaft 148 therethrough. One end of axle 170 may be connected to sheath end wall 166 and the other end may be connected to proximal retainer 142, the connection being made so that at least one end of the axle is freely rotatable. Thus, for example, one end of axle 170 may be fixedly connected to sheath end wall 166, while the other end is rotatably connected to retainer 142. Optionally, the rotatable end of axle 170 may be journaled in a receiving element, such as roller bearing 175, disposed in the retainer 142. A flange 172 at an end of axle 170 may maintain the assembly between the axle and roller bearing 175. It will be appreciated, of course, that in a variant hereof, one end of the axle may be fixedly connected to retainer 142 and the end of the axle connected to end wall 166 may be rotatable, and that the roller bearing 175 or other retaining element may be mounted to the end wall 166 to facilitate rotation.

Device 100 may further include a locking rod 180 which extends along the length of proximal sheath 160 in a position offset from the central axis thereof. A compression spring 182 may be assembled around the distal end of rod 180 and constrained between an end member 185 of a spring retainer 184 mounted to the sheath end wall 166 and a stop ring 186 fixedly mounted to the locking rod. Spring 182 may bias locking rod 180 distally so that the distal end thereof projects through an aperture 188 in the sheath end wall 166, and into one of a series of recesses 189 in the proximal retainer 142. The engagement of locking rod 180 in one of recesses 189 fixes the rotational position of distal sheath 162 relative to the proximal sheath 160. Preferably, retainer 142 includes an appropriate number of recesses 189 along its outer periphery to lock the distal sheath 162 at any number of desired rotational angles relative to the proximal sheath 160. The size of spring 182 is selected so that locking rod 180 may be retracted by an amount sufficient to move the distal end of the rod out from a recess 189, thereby freeing the distal sheath 162 to rotate relative to proximal sheath 160.

In an initial fully closed position, shown in FIG. 3, the proximal sheath 160 and the distal sheath 162 may share a common longitudinal axis. Upon retraction of locking rod 180, the distal sheath 162 may be rotated relative to the proximal sheath 160 about the longitudinal axis of axle 170. As a result of the oblique angle defined between the two sheaths, rotation of the distal sheath 162 relative to the proximal sheath 160 will cause the longitudinal axis of the distal sheath to deflect away from coaxial alignment with the longitudinal axis of the proximal sheath.

The angle formed by the intersection of the longitudinal axes of the distal sheath 162 and the proximal sheath 160 increases or decreases as the sheaths are rotated relative to one another. When the end wall 166 of the proximal sheath 160 and the proximal end 164 of the distal sheath 162 are both flat and disposed at the same oblique angle to the longitudinal axes of their respective sheaths, the maximum angular displacement between the longitudinal axes will occur when the sheaths have been rotated from their coaxial configuration 180° relative to one another. The amount of angular displacement achieved preferably is at least about 15°. However, the angular displacement should be sufficient to enable the distal sheath 162 to be substantially axially aligned with the native aortic annulus. When the oblique angles at which the proximal end 164 of distal sheath 162 and the sheath end wall 166 are disposed are about equal, the maximum angular displacement that may be achieved will be about twice the oblique angle. Thus, for example, when the oblique angle is about 15°, the maximum angular displacement achieved when the distal sheath 162 is rotated 180° relative to the proximal sheath 160 will be about 30°.

It will be appreciated that the maximum angular displacement which device 100 may achieve may be increased by increasing the oblique angle of at least one of proximal end 164 or end wall 166 relative to the longitudinal axes of their respective sheaths. However, if the oblique angles are not equal, coaxial alignment will be difficult to achieve, if achievable at all.

In order for distal sheath 162 to become angularly displaced relative to proximal sheath 160, it is necessary for inner shaft 148 to be able to bend at the interface between the sheaths. It will be appreciated that this may be accomplished in any number of ways while still maintaining the ability of inner shaft 148 to control the longitudinal movement of distal sheath 162 relative to proximal sheath 160. For example, inner shaft 148 may be formed from first and second substantially rigid portions 148a, 148b joined together by a relatively stiff spring, a length of polymer tubing or another flexible tubular material 149 which will enable the rigid portions to move at substantially any angle relative to one another. Alternatively, the rigid portions may be joined together by a ball and socket joint (not shown) which similarly will provide for unlimited angular displacement between the rigid shaft lengths. Thus, the substantially rigid portions of shaft 148 may be connected by any joint that will enable the portions of the shaft to be deflected from substantially coaxial alignment, but that will still retain sufficient strength in both compression and tension to displace distal sheath 162 longitudinally relative to proximal sheath 160.

Figure 1:
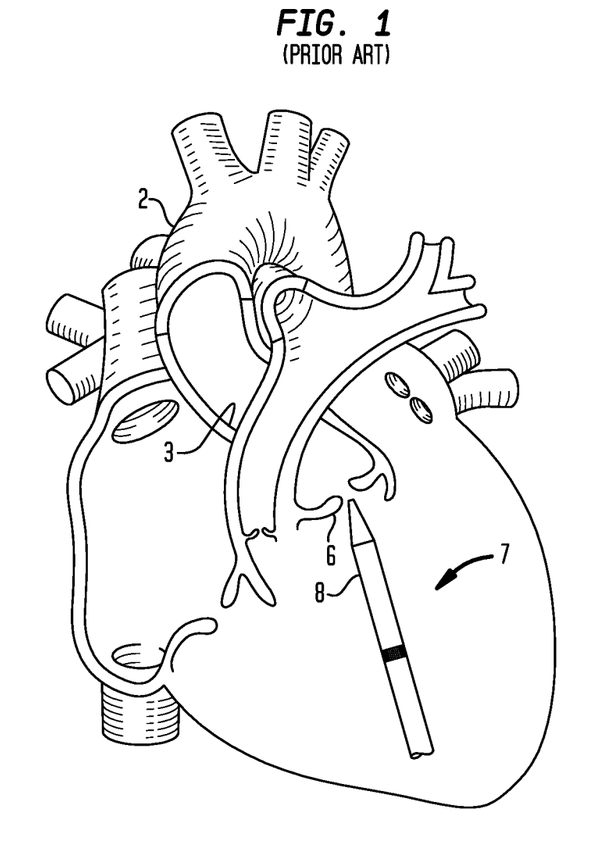
FIG. 1 is a diagrammatic view showing the use of a conventional transapical delivery device to deliver a collapsible prosthetic heart valve to the aortic valve annulus.

The delivery device 100 may be inserted into a patient during a minimally invasive surgical procedure such as, for example, to replace a native heart valve with a collapsible prosthetic heart valve. During a transapical surgical procedure to replace the native aortic valve, device 100 may be locked in the straight or coaxial position and inserted through the apex of the heart and the left ventricle and advanced toward the native aortic valve. As the distal tip 140 of device 100 contacts the aortic annulus 6, locking rod 180 may be retracted until the distal end thereof is fully removed from recess 189 in proximal retainer 142, freeing the distal sheath 162 for rotation relative to the proximal sheath 160. As the proximal sheath 160 is rotated by the user, friction between distal tip 140 and the native valve annulus 6 will inhibit the rotation of distal sheath 162. As a result, proximal sheath 160 will rotate relative to distal sheath 162, thereby deflecting the longitudinal axis of distal sheath 162 relative to the longitudinal axis of proximal sheath 160. Locking rod 180 may then be released, whereupon spring 182 will bias the rod through aperture 188 and into a different recess 189 in proximal retainer 142. The creation of an angle between proximal sheath 160 and distal sheath 162 will enable the distal tip 140 to be directed away from the native valve annulus 6 and the interior wall 3 of aortic arch 2, and will enable device 100 to be advanced further into and through the native valve annulus. As device 100 is advanced, the distal tip 140 will again approach the interior wall 3 of aortic arch 2, and the locking rod 180 may again be retracted and proximal sheath 160 rotated relative to distal sheath 162 to increase the angle between the longitudinal axes of the sheaths. Locking rod 180 may then be released to engage a different recess 189, locking the sheaths relative to one another in this new position. This procedure may be repeated as device 100 is advanced through aortic annulus 6 until distal sheath 162 is substantially in axial alignment with the native valve annulus and sufficiently advanced therethrough for deployment of valve 50. Following deployment, the procedure may be reversed, perhaps with fewer increments, to remove device 100 from the patient. Although the foregoing describes incremental rotations between distal sheath 162 and proximal sheath 160 as device 100 is advanced into and through aortic annulus 6, it will be appreciated that the procedure may be accomplished with only a single 180° rotation of the sheaths relative to one another. In such event, device 100 may be configured so as to be lockable in only two positions, namely, a coaxial position and a position rotated 180° from the coaxial position.

Figure 5:
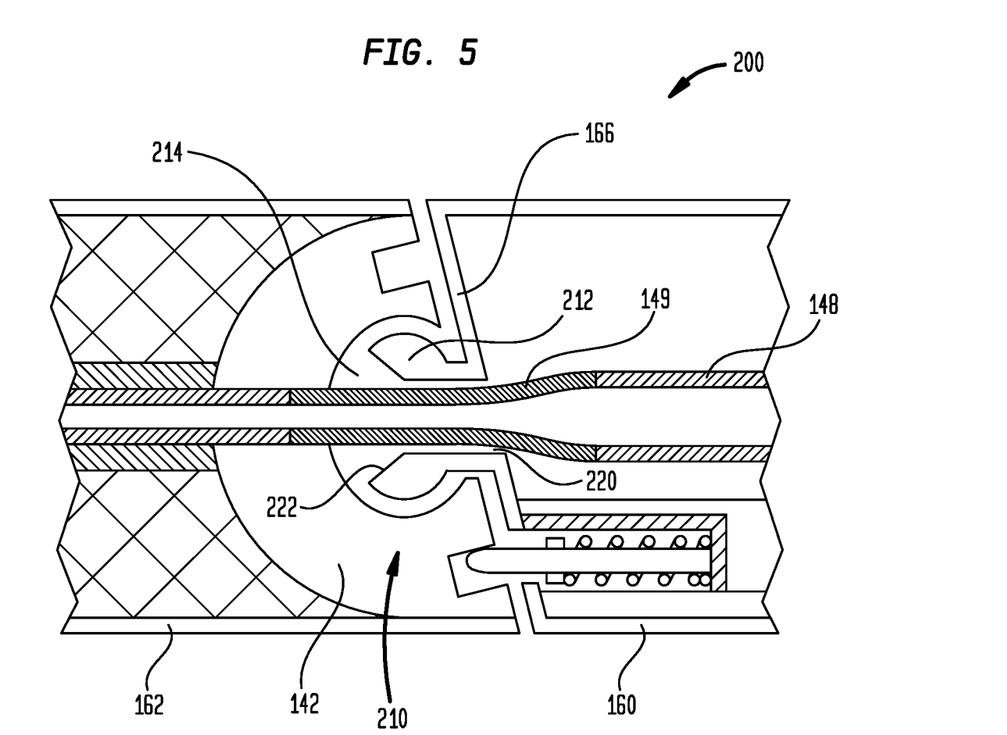
FIG. 5 is a cross-sectional plan view of a portion of a delivery device in accordance with another embodiment of the present invention, shown in a substantially straight configuration.
Figure 6:
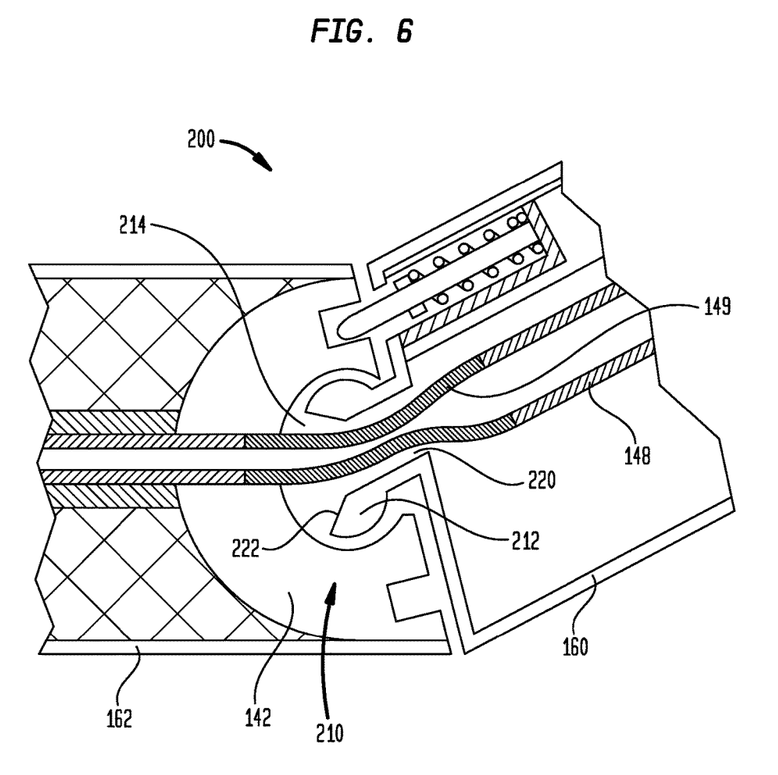
FIG. 6 is a cross-sectional plan view of the portion of the delivery device of FIG. 5, shown in a deflected configuration.

An alternate embodiment of a delivery device 200 is shown in FIGS. 5 and 6. Delivery device 200 is substantially the same as delivery device 100 described above. However, rather than employing an axle 170 to rotatably connect distal sheath 162 to proximal sheath 160, device 200 employs a ball and socket connection 210. Thus, a ball 212 may project from the end wall 166 of proximal sheath 160 and be received within a socket 214 formed in proximal retainer 142. Ball 212 may include a throughbore 220 sized to slidably receive inner shaft 148 therethrough. At the free end of ball 212, throughbore 220 may have an outwardly flared or chamfered surface 222. Surface 222 will accommodate the bending of inner shaft 148 as distal sheath 162 is deflected relative to proximal sheath 160, and will prevent the flexible portion 149 of the shaft from kinking or becoming pinched closed as shaft 148 bends. In a variant hereof, the components of ball and socket connection 210 may be reversed. That is, ball 212 may be connected to proximal retainer 142 and socket 214 may be formed in or connected to sheath end wall 166.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for implanting a prosthetic heart valve into a patient, the method comprising:
    inserting a delivery device into a vasculature of a patient to a position adjacent to a curvate section of the vasculature of the patient, the delivery device having a prosthetic heart valve located therein and including a shaft having proximal and distal ends and a tip attached to the shaft and having proximal and distal ends, the distal end of the shaft having a distal end surface and the proximal end of the tip having a proximal end surface;
    rotating a tip relative to the shaft from a first position in which a longitudinal axis of the tip is collinear with a longitudinal axis of the shaft to a second position in which the longitudinal axis of the tip forms an oblique angle with the longitudinal axis of the shaft, the proximal end surface of the tip confronting and being substantially parallel to the distal end surface of the shaft during rotation of the tip from the first position to the second position, and each of the proximal end surface of the tip and the distal end surface of the shaft being oriented at an oblique angle relative to the longitudinal axis of the shaft; and
    deploying the prosthetic heart valve from the delivery device.

2. The method of claim 1, the method further comprising:
disengaging a locking rod attached to the shaft from the tip such that the tip becomes rotatable relative to the shaft.

3. The method of claim 2, wherein the locking rod is movable in the shaft between an extended position in which the locking rod is engaged with the tip and a retracted position in which the locking rod is disengaged from the tip.

4. The method of claim 1, wherein the delivery device is inserted into the patient over a guide wire passing through a shaft lumen extending between the proximal end and the distal end of the shaft and a tip lumen extending between proximal and distal ends of the tip, the shaft lumen being in communication with the tip lumen.

5. The method of claim 1, wherein the delivery device is inserted into the vasculature of the patient such that rotation of the shaft does not rotate the tip.

6. The method of claim 1, wherein the tip is rotated relative to the shaft about a longitudinal axis of an axle interconnecting the shaft and the tip.

7. The method of claim 1, wherein the tip is rotated relative to the shaft about a ball-and-socket combination interconnecting the shaft and the tip.

8. The method of claim 1, further comprising advancing the tip sufficiently through a native valve annulus of the heart valve of the patient for deployment of the prosthetic heart valve, wherein the prosthetic heart valve is deployed at or near the native valve annulus.

9. A method for delivering an implantable medical apparatus into a patient, the method comprising:
inserting a delivery device having a medical apparatus held thereby into a patient, the delivery device further having a shaft and a tip, a proximal end of the tip operatively connected to a distal end of the shaft, the distal end of the shaft having a distal end surface and the proximal end of the tip including a proximal end surface;
rotating the tip relative to the shaft from a first position in which a longitudinal axis of the tip is collinear with a longitudinal axis of the shaft to a second position in which the longitudinal axis of the tip forms an oblique angle with the longitudinal axis of the shaft, the proximal end surface of the tip confronting and being substantially parallel to the distal end surface of the shaft during rotation of the tip from the first position to the second position, and each of the proximal end surface of the tip and the distal end surface of the shaft being oriented at an oblique angle relative to the longitudinal axis of the shaft; and
moving a sheath connected to the tip distally away from the distal end of the shaft from a first condition in which the sheath encloses a compartment of the tip to a second condition in which the sheath exposes the compartment for deployment of the medical apparatus into the patient.

10. The method of claim 9, wherein the tip is rotated 180 degrees relative to an axis perpendicular to a flat surface of the shaft confronting the tip to form the oblique angle.

11. The method of claim 9, wherein the tip is rotated relative to the shaft about a longitudinal axis of an axle interconnecting the shaft and the tip.

12. The method of claim 11, wherein the longitudinal axis of the axle is at an oblique angle relative to the longitudinal axis of any one of the shaft and the tip.

13. The method of claim 9, wherein the tip is rotated relative to the shaft about a ball-and-socket combination interconnecting the shaft and the tip.

14. The method of claim 9, wherein the delivery device is inserted into the patient over a guide wire passing through a shaft lumen extending between a proximal end and the distal end of the shaft and a tip lumen extending between proximal and distal ends of the tip, the shaft lumen being in communication with the tip lumen.

15. The method of claim 9, the method further comprising disengaging a locking rod attached to the shaft from the tip such that the tip becomes rotatable relative to the shaft.

16. The method of claim 15, wherein the locking rod is movable in the shaft between an extended position in which the locking rod is engaged with the tip and a retracted position in which the locking rod is disengaged from the tip.

17. The method of claim 9, wherein the sheath is movable with the tip between the first position and second position.

18. The method of claim 9, wherein the delivery device is inserted into the patient such that rotation of the shaft does not rotate the tip.

19. A method for delivering an implantable medical apparatus into a patient, the method comprising:
inserting a delivery device into a patient, the delivery device having a shaft and a tip connected by an axle to the shaft such that a proximal end surface of the tip confronts a distal end surface of the shaft and having a medical apparatus held thereby;
rotating the tip relative to the shaft from a first position in which a longitudinal axis of the tip is collinear with a longitudinal axis of the shaft to a second position in which the longitudinal axis of the tip forms an oblique angle with the longitudinal axis of the shaft, the proximal end surface of the tip remaining substantially parallel to the distal end surface of the shaft during rotation of the tip from the first position to the second position; and
deploying the medical apparatus from the delivery device.

20. A method for delivering an implantable medical apparatus into a patient, the method comprising:
inserting a delivery device into a patient, the delivery device having a shaft and a proximal end of the tip operatively connected to a distal end of the shaft and having a medical apparatus held thereby;
disengaging a locking rod attached to the shaft from the tip such that the tip becomes rotatable relative to the shaft;
rotating the tip relative to the shaft from a first position in which a longitudinal axis of the tip is collinear with a longitudinal axis of the shaft to a second position in which the longitudinal axis of the tip forms an oblique angle with the longitudinal axis of the shaft; and
moving a sheath connected to the tip distally away from the distal end of the shaft from a first condition in which the sheath encloses a compartment of the tip to a second condition in which the sheath exposes the compartment for deployment of the medical apparatus into the patient.

21. The method of claim 20, wherein the locking rod is movable in the shaft between an extended position in which the locking rod is engaged with the tip and a retracted position in which the locking rod is disengaged from the tip.

* * * * *